United States Patent
Elahinia et al.

(10) Patent No.: US 8,591,559 B2
(45) Date of Patent: Nov. 26, 2013

(54) FIXATION ASSEMBLY HAVING AN EXPANDABLE INSERT

(75) Inventors: Mohammad Elahinia, Toledo, OH (US); Vijay K. Goel, Holland, OH (US); Majid Tabesh, Toledo, OH (US)

(73) Assignee: The University of Toledo, Toledo, OH (US)

( * ) Notice: Subject to any disclaimer, the term of this patent is extended or adjusted under 35 U.S.C. 154(b) by 261 days.

(21) Appl. No.: 13/126,017

(22) PCT Filed: Oct. 27, 2009

(86) PCT No.: PCT/US2009/062267
§ 371 (c)(1),
(2), (4) Date: Aug. 19, 2011

(87) PCT Pub. No.: WO2010/051289
PCT Pub. Date: May 6, 2010

(65) Prior Publication Data
US 2012/0116465 A1    May 10, 2012

Related U.S. Application Data

(60) Provisional application No. 61/108,644, filed on Oct. 27, 2008.

(51) Int. Cl.
*A61B 17/86* (2006.01)
(52) U.S. Cl.
USPC ........................................................ 606/310
(58) Field of Classification Search
USPC ........... 606/300–321; 411/383, 411, 412, 470
See application file for complete search history.

(56) References Cited

U.S. PATENT DOCUMENTS

| | | | | |
|---|---|---|---|---|
| 2,430,158 A | * | 11/1947 | Cass | 301/35.61 |
| 3,477,337 A | * | 11/1969 | Racki | 411/28 |
| 5,092,727 A | * | 3/1992 | Moghe | 411/411 |
| 5,417,712 A | * | 5/1995 | Whittaker et al. | 606/232 |
| 5,536,126 A | * | 7/1996 | Gross | 411/411 |
| 5,636,549 A | * | 6/1997 | Devenyi | 74/424.75 |
| 5,662,294 A | * | 9/1997 | Maclean et al. | 244/219 |
| 5,683,460 A | * | 11/1997 | Persoons | 606/60 |
| 5,779,707 A | * | 7/1998 | Bertholet et al. | 606/75 |
| 5,849,004 A | * | 12/1998 | Bramlet | 606/232 |
| 5,868,747 A | * | 2/1999 | Ochoa et al. | 606/300 |
| 6,276,883 B1 | * | 8/2001 | Unsworth et al. | 411/324 |
| 6,325,805 B1 | | 12/2001 | Ogilvie et al. | |

(Continued)

FOREIGN PATENT DOCUMENTS

| | | |
|---|---|---|
| DE | 19731298 A1 | 11/1999 |
| WO | 2007035200 A3 | 3/2007 |
| WO | 2010051289 A1 | 5/2010 |

OTHER PUBLICATIONS

PCT International Search Report and the Written Opinion, PCT/US2009/062267 filed Oct. 27, 2009, dated Dec. 15, 2009.

(Continued)

*Primary Examiner* — Kevin T Truong
*Assistant Examiner* — Zade Coley
(74) *Attorney, Agent, or Firm* — MacMillan, Sobanski & Todd, LLC

(57) ABSTRACT

A fixation assembly having one or more insertions member that include one or more expandable and retractable anchoring inserts positioned along at least a portion of the insertion member and methods of use thereof are disclosed.

16 Claims, 6 Drawing Sheets

(56) References Cited

U.S. PATENT DOCUMENTS

| | | | |
|---|---|---|---|
| 6,530,933 B1* | 3/2003 | Yeung et al. | 606/151 |
| 6,551,319 B2 | 4/2003 | Lieberman | |
| 6,668,688 B2 | 12/2003 | Zhao et al. | |
| 6,862,470 B2 | 3/2005 | Burbank et al. | |
| 6,926,483 B2* | 8/2005 | Hesse et al. | 411/36 |
| 7,008,453 B1 | 3/2006 | Michelson | |
| 7,165,925 B2* | 1/2007 | Unsworth et al. | 411/324 |
| 7,297,162 B2 | 11/2007 | Mujwid | |
| 7,879,036 B2* | 2/2011 | Biedermann et al. | 606/62 |
| 8,048,134 B2* | 11/2011 | Partin | 606/320 |
| 2002/0055742 A1* | 5/2002 | Lieberman | 606/73 |
| 2002/0156473 A1* | 10/2002 | Bramlet et al. | 606/62 |
| 2004/0082956 A1* | 4/2004 | Baldwin et al. | 606/73 |
| 2005/0187555 A1 | 8/2005 | Biedermann et al. | |
| 2006/0129147 A1* | 6/2006 | Biedermann et al. | 606/61 |
| 2006/0133961 A1 | 6/2006 | Lim et al. | |
| 2007/0198018 A1* | 8/2007 | Biedermann et al. | 606/73 |
| 2007/0293866 A1* | 12/2007 | Stoeckel et al. | 606/72 |
| 2008/0234756 A1 | 9/2008 | Sutcliffe et al. | |
| 2008/0243264 A1 | 10/2008 | Fonte | |
| 2008/0262629 A1 | 10/2008 | Fonte | |
| 2009/0005782 A1* | 1/2009 | Chirico et al. | 606/63 |

OTHER PUBLICATIONS

PCT International Preliminary Report on Patentability, PCT/US2009/062267 filed Oct. 27, 2009, dated May 12, 2011.

* cited by examiner

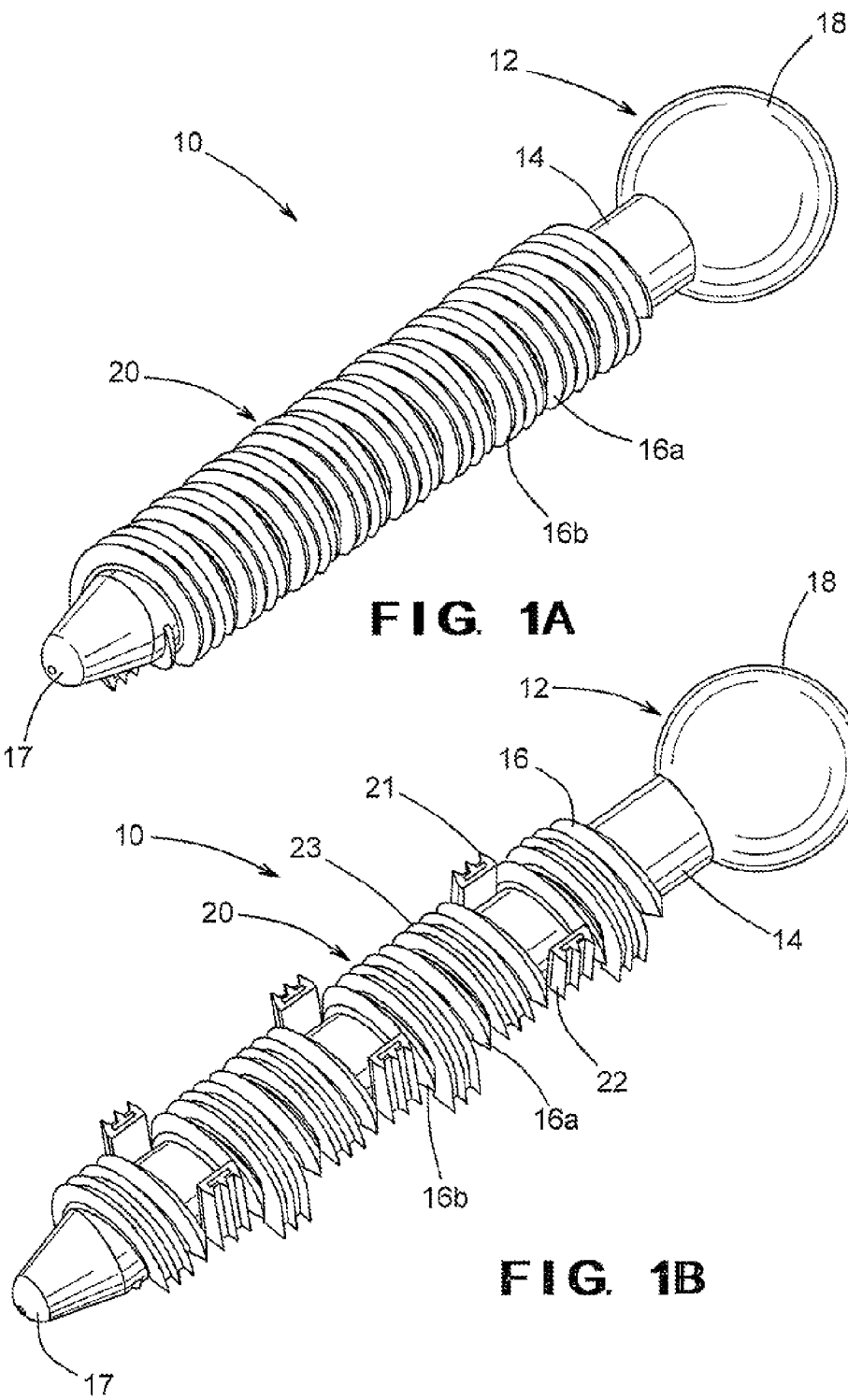

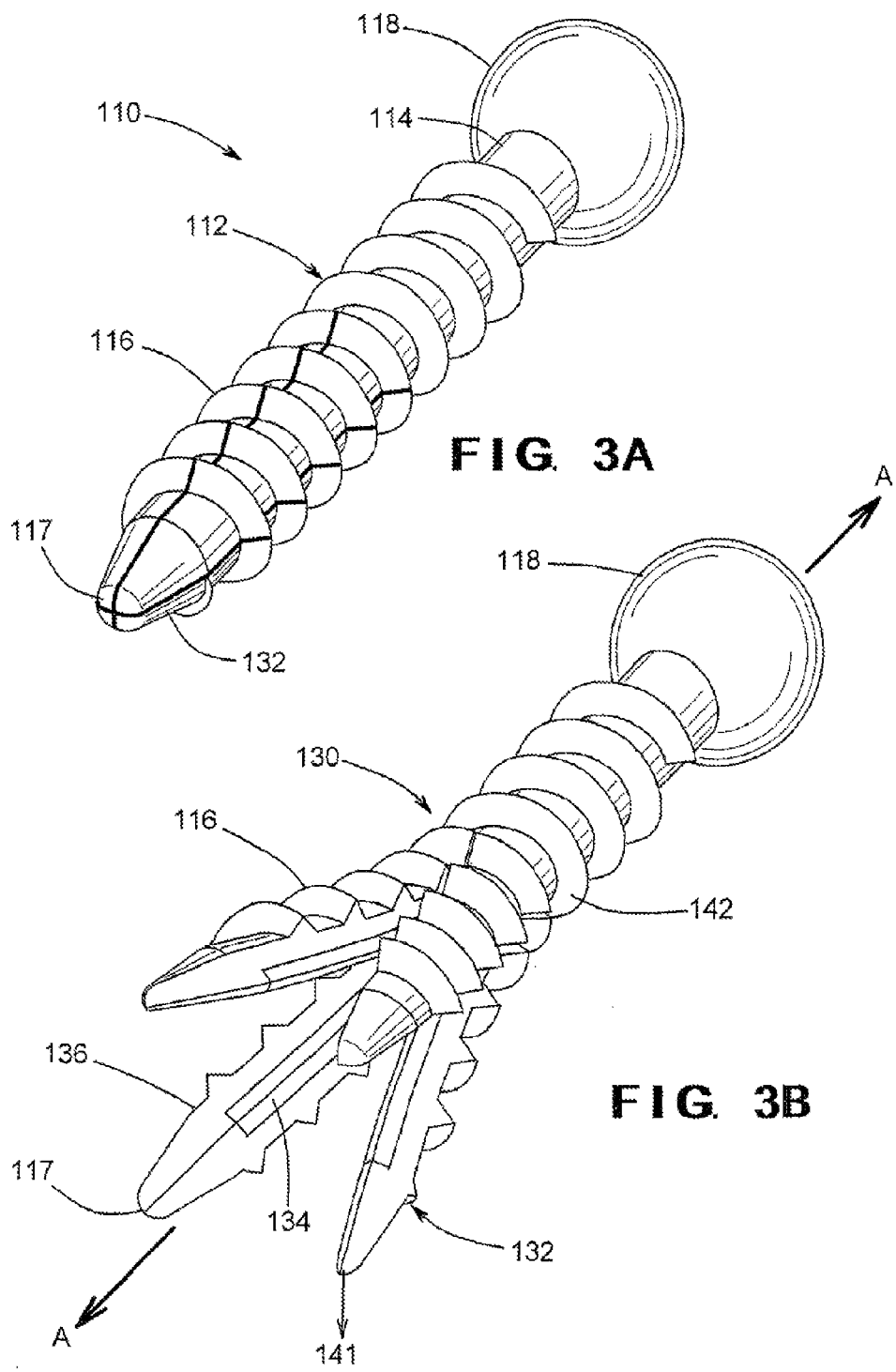

FIXATION ASSEMBLY HAVING AN EXPANDABLE INSERT

CROSS-REFERENCE TO RELATED APPLICATIONS AND STATEMENT REGARDING SPONSORED RESEARCH

The present invention claims the benefit of the PCT/US2009/062267 filed Oct. 27, 2009, which claims priority to the provisional patent application Ser. No. 61/108,644 filed Oct. 27, 2008. This invention was made with no Government support and the Government has no rights in this invention.

FIELD OF INVENTION

In a broad aspect, the present invention relates to bone fixation devices that are especially useful in affixing instrumentation to compromised bone that is weakened or damaged. It is to be understood that while the following explanation is directed to one embodiment directly related to bone fixation assemblies (such as spinal bone fixation assemblies), that the present invention is useful in a wide variety of applications in addition to the specific medical indications described herein.

BACKGROUND OF THE INVENTION

As our population ages, more people develop bone and/or spinal problems. Metabolic bone diseases such as osteoporosis, osteomalacia, and Paget's disease are usually associated with osteoporotic or soft skeleton, especially in elderly patients.

In particular, osteoporosis, a progressive metabolic bone disease, affects 10 million Americans. For example, approximately 30% of postmenopausal white women in the United States have osteoporosis, and 16% have osteoporosis of the lumbar spine in particular.

Initially, osteoporosis primarily involves the inner layer of bone, the cancellous portion. In the early stages of osteoporosis, the number and strength of trabeculae diminish, weakening the structural stability of the bone. In later stages, osteoporosis will weaken the cortical portion of the bone also. Endocrine, metabolic, genetic, and nutritional disorders further contribute to the development of osteoporosis. Related risks include long-term corticosteroid use, chemotherapy, radiation therapy, age and gender, genetics, and unhealthy lifestyle choices. Similar devastation to vertebral structures can be caused by metastatic spinal disease. For example, other processes, such as cancer, can alter the normal architecture of cancellous bone. By invading and replacing bone marrow, cancers can weaken individual bones in the same manner that osteoporosis does. Surgery is often presented as an option to treat such patients by providing support and/or stability to the patient's bones. While such procedures are often successful, as patients live longer, their risk of osteoporosis increases. Consequently, the presence of osteoporotic bone is an increasingly common challenge to orthopedic surgeons.

In spinal surgery, for example, screws are used in fixation procedures to treat spinal instability by positioning supporting instrumentation along the spine. The use of spinal instrumentation in osteoporotic patients is often complicated by this problem of hardware pull-out or loosening. This complication may occur during surgery, while manipulating the instrumentation, or at any time after surgery. This is a special concern since screws that are inserted in to osteoporotic vertebrae will compress the cancellous bone within the vertebrae whenever the spine is loaded. The cancellous bone will continually be compressed until the screw contacts the endplates of the vertebrae or until enough bone is compressed and a stable column is formed against the screw that prevents its further displacement.

Often, screw failure in osteoporotic bone involves compaction of enclosing cancellous bone during loading; unlike failure in dense bone, which entails screw bending without bone failure. If screw loosening occurs late after surgery, the patient may need either revision of the instrumentation or supplementation with an anterior fusion incurring complications and high costs. Therefore, selection of appropriate instrumentation and a means to augment it is crucial in osteoporotic patients.

Therefore, there is a need for improved fixation assemblies and methods of using the same.

BRIEF SUMMARY OF THE INVENTION

In a broad aspect, there is provided herein a fixation assembly having at least one insertion member that includes one or more expandable and retractable anchoring inserts positioned along at least a portion of the insertion member.

In another broad aspect, there is provided herein a fixation assembly having an insertion member having a shaft and one or more expandable and retractable anchoring inserts positioned along at least a portion of the shaft.

In another broad aspect, there is provided herein a fixation assembly that includes a screw having a shaft with a straight, transverse, or helical ridge, groove or thread formed on at least a portion of an outer surface of the shaft; the screw having a leading (distal) end and a head at an opposing (proximal) end. One or more expandable and retractable anchoring inserts are positioned along at least to portion the shaft between or across one or more adjacent threads.

In certain non-limiting embodiments, the insert comprises one or more expandable thread inserts capable of expanding and retracting in response to changes in temperature.

In certain non-limiting embodiments, the insert is responsive to changes in body temperature and is actuated due to body heat within the subject and is capable of being retracted by being exposed to heat or cold. That is, in certain embodiments, the insert can be retracted by lowering the temperature or cryoenergy.

In certain non-limiting embodiments, at least a portion of the insert comprises at least one shape memory and/or superelastic materials. In certain embodiments, the shape memory material can be a shape memory alloy. In certain embodiments, the insert can have a first end and a second end that are separated by a central portion, such that the first and second ends are capable of being separated from adjacent positions when the insert is exposed to an appropriate change in temperature.

In another broad aspect, there is provided herein a fixation assembly where the insert has a retractor segment at least partially in contact with a protractor segment. At least a portion of the protractor segment can be comprised of a material that expands or contracts in response to a change in temperature, and/or at least a portion of the retractor segment can be comprised of a shape memory material which has an austenite transformation temperature different from the temperature at which the protractor expands or contracts.

In certain non-limiting embodiments, at least a portion of the retractor segment is activated by heating the insert.

In certain non-limiting embodiments, the retractor segment defines a channel that receives a least a portion of the protractor segment.

In certain non-limiting embodiments, the shaft has a cylindrical shape that tapers to a point at one end. Also, in certain non-limiting embodiments, the head has a shape by which the screw can be connected to a 360 degree fixation rod. In certain non-limiting embodiments, the threads have any desired pitch and are spaced along the shaft at any desired spacing.

In certain non-limiting embodiments, the fixation assembly comprises a bone fixation assembly. Also, in certain non-limiting embodiments, the fixation assembly comprises a pedicle screw bone fixation assembly.

In yet another broad aspect, there is provided herein a fixation assembly having a screw portion having a shaft with a straight, transverse, or helical ridge, groove or thread formed on an outer surface of the shaft, the screw portion having a leading (distal) end and a head at an opposing (proximal) end. At least a portion of the shaft can be comprised of an anchoring member. The anchoring member can have one or more generally longitudinally or transversely extending legs that define at least a part of the shaft; at least one of the legs has an elastic exterior section at least in partial contact with an interior leg that is comprised of an expandable material.

In certain non-limiting embodiments, the exterior section includes threads on an exterior surface and defines at least one channel on an interior surface, the channel being configured to receive at least a portion of the interior leg.

In certain non-limiting embodiments, one or more of the interior legs are capable of expanding at body temperature and are actuated due to body heat within the subject.

In certain non-limiting embodiments, at least a distal portion of the exterior leg is capable of moving in a generally radially or longitudinally outward direction away from an axis defined by the shaft upon exposure to a change in temperature.

In still another broad aspect, there is provided herein a method of inserting a fixation assembly, comprising a fixation assembly of any of the preceding claims; inserting at least portion of the fixation assembly into an object; exposing at least a portion of the fixation assembly to a change in temperature sufficient to cause a least a portion of the fixation assembly to change dimensionally, whereby at least a portion of the fixation assembly is secured within the object. In certain non-limiting embodiments, the object can comprise bone. Also, in certain non-limiting embodiments, the object comprises osteoporotic bone.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

FIG. 1A is a perspective view of a pedicle screw assembly prior to insertion.

FIG. 1B is a perspective view of a pedicle screw assembly after insertion.

FIG. 3A is a perspective view of another embodiment of a pedicle screw assembly in a first, and contracted, position.

FIG. 3B is a perspective view of an expanded exterior portion of the embodiment of FIG. 3A.

DETAILED DESCRIPTION OF THE PREFERRED EMBODIMENT(S)

Figure 2A:
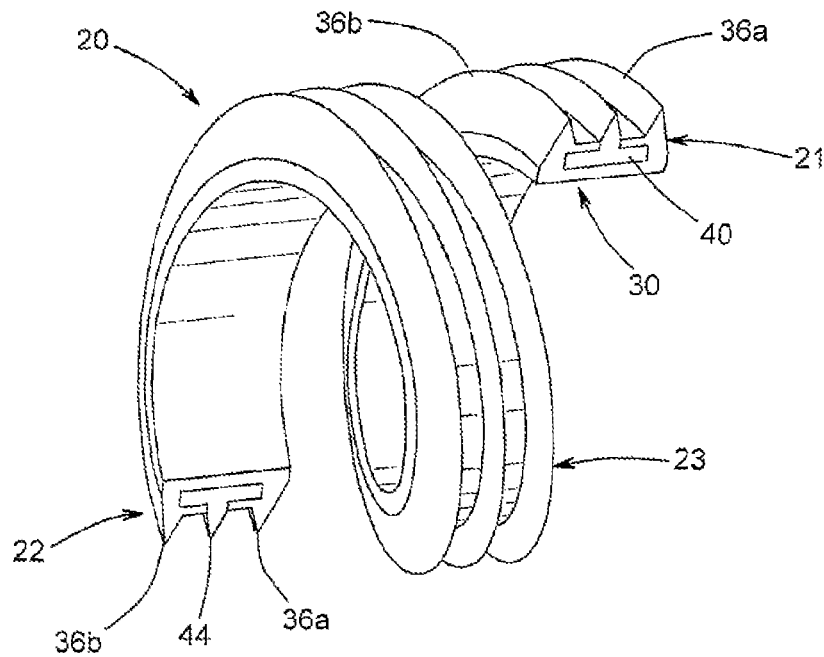
FIG. 2A is a perspective view of an anchoring insert of a pedicle screw assembly shown in a first, and contracted, position.

In a broad aspect, there is provided herein a fixation assembly that incorporates expandable members that aid in anchoring the fixation assembly into an object. In certain embodiments, the expandable members are comprised of a material that is responsive to changes in the environment in which it is placed.

In another broad aspect, there is provided herein a fixation assembly that addresses the problem of screw loosening after placement in a subject. The bone fixation assemblies provide a solution that can be used in osteoporotic patients as well as in non-osteoporotic patients.

In a particular aspect, the fixation assembly can expand into the areas of bone loss in order to maintain consistent mechanical contact between the fixation assembly and the bone into which it is inserted.

In particular embodiments, the fixation assembly has one or more expandable members that are comprised, at least in part, of materials that are reactive to changes in temperature. In one embodiment, the expandable members are comprised of shape memory alloy (SMA) materials.

SMA materials have distinct material properties that include a shape memory effect which allows the SMA material to return to its original shape by simply increasing the temperature of the SMA material. With certain SMA materials, the SMA material returns to its original shape by simply increasing the temperature within a strain of up to 8%.

Another distinct material property of SMA materials is their superelasticity which allows the formation of an elastic behavior, but under a level of values more significant than those of the classic metals or alloys. This characteristic of the SMA materials allows the fixation assembly to be readily recoverable after insertion if such situation would arise. The thermo-mechanical properties of SMA materials, especially the equiatomic intermetallic compound of NiTi, provide a solution for some of the biomechanical issues encountered in orthopedics.

It is to be understood that while the examples presented herein are directed to enhanced pedicle screw performance, the present invention is readily applicable to many other forms of bone fixation assemblies and, as such, are capable of being implemented in any situation where bone degradation enforces fixation difficulties. In one particular aspect, the bone fixation assemblies are useful to compensate for osteoporosis adverse effects on spinal implants. The temperature responsiveness characteristic of the SMA bone fixation assemblies allows the surgeon to both insert and/or remove the fixation assembly screw as needed during and after the surgery.

For ease of illustration, the present invention will now be discussed in detail with respect to a pedicle screw fixation assembly to illustrate some of the biomechanical issues encountered in orthopedics. For example, the problem of pedicle screw loosening and back-out due to osteoporosis is substantially alleviated with the fixation assembly described herein. Again, it should be noted that although the embodiments illustrated herein specifically describe enhanced pedicle screw performance, other embodiments of bone fixation assemblies are capable of being implemented in any situation where hone degradation enforces fixation difficulties.

Referring now to FIG. 1A and FIG. 1B, there is shown a fixation assembly 10 that includes a screw 12 and one or more inserts 20. The screw 12 generally has a shaft 14 and helical ridges, grooves or threads 16 formed along at least a portion of the shaft 14. The threads 16 can have any desired pitch and can be spaced along the shaft 14 at any desired spacing. Portions of the shaft 14 that are between adjacent threads 16a, 16b are designed in the Figures as shaft portions 15.

The screw 12 also has a first or leading (distal) end 17 and a head 18 at an opposing (proximal) end. It is to be understood that, in certain embodiments, the shaft 14 can be a cylindrical shaft which can taper to a point at the end 17, while the head 18 can have any desired suitable shape by which the screw 12 can be rotated.

In the embodiment show in FIG. 1A and FIG. 1B, the fixation assembly 10 includes a plurality of anchoring inserts 20. For ease of illustration and explanation, while multiple segmented inserts 20 are shown, one insert 20 will be described in detail herein. It should be understood that, in certain embodiments, each insert 20 can have substantially the same dimensions (length, width, cross-sectional shape, overall shape, and the like), while in other embodiments; one or more of the inserts 20 can have different dimensions.

The insert 20 is positioned along the shaft 14 and is positioned between adjacent threads 16a and 16b. The insert 20 is at least partially in contact with the shaft portion 15, as further described herein.

In a particular embodiment, at least one insert 20 is capable of expanding at body temperature and are actuated (i.e., expanded) due to body heat within the subject. Also, in certain embodiments, the insert 20 is also capable of being retracted by being exposed to a change in temperature, as further described herein.

Once expanded, as shown in FIG. 1B, the insert 20 aids in providing a means of gripping adjacent bone (not shown) and acts as a firm anchor point within the bone. The expanded insert 20 can compensate for any threads 16 that might engage adjacent bone and/or that might not be exposed to a load evenly. With the expanded insert 20, the fixation assembly 10 provides a more even load sharing and improved retention within the bone.

That is, once the fixation assembly 10 is positioned in the bone, at least a portion of the insert 20 expands as the insert 20 responds the subject's body temperature. Also, in certain embodiments, once the fixation assembly 10 is in situ, the insert 20 can continue to augment the contact, or purchase, of the fixation assembly 10 to the adjacent bone as the bone continues to deteriorate and/or goes through osteoporosis. That is, the insert 20 can continue to expand (in response to body temperature) into the adjacent areas of the bone that are degraded by osteoporosis and/or the irritating presence of the fixation assembly 10 itself.

Figure 2B:
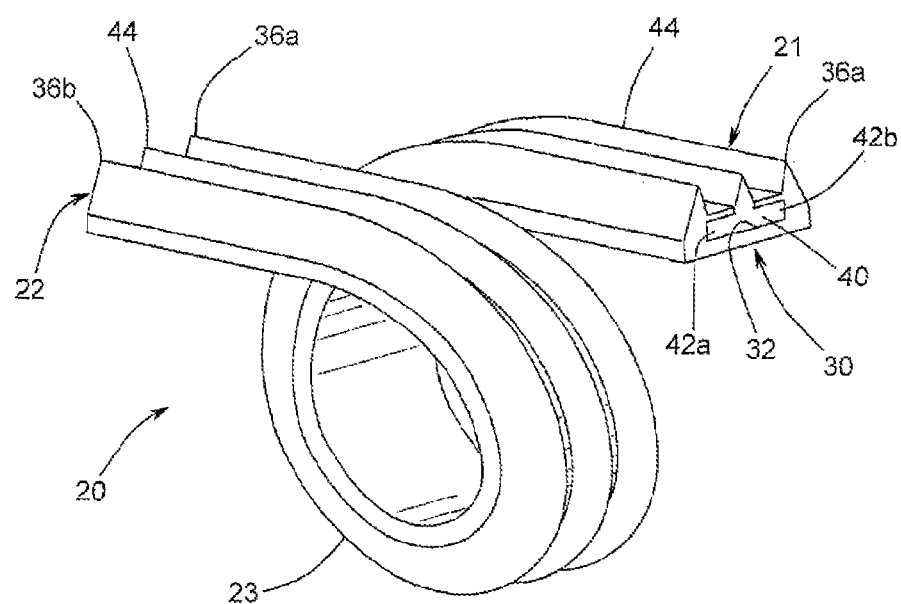
FIG. 2B is a perspective view of an anchoring insert of a pedicle screw assembly in a second, and expanded, position.

FIG. 2A shows one embodiment of an expandable insert 20 in a non-deformed, or contracted, configuration. FIG. 2B shows the embodiment of FIG. 2A in a deformed, or expanded, configuration. The insert 20 generally has a first end 21 and a second end 22 that are separated by a central portion 23. The insert 20 generally has a coiled, or spiral, configuration such that the insert 20 can be positioned between adjacent threads 16a, 16b (as seen in FIGS. 1A-1B).

When the insert 20 is in the first, contracted configuration, the first and second ends 21 and 22, respectively, are disposed close to the shaft portions 15, as shown in FIG. 1A. When the insert 20 is in the second, expanded configuration, the first and second ends 21 and 22, respectively, are disposed at spaced apart relationship with respect to the shaft portions 15. The insert 20 can have a generally helical shape where the first and second opposing ends are configured to be expanded in a tangential manner with respect to the shaft 14 when exposed to a change in temperature.

Referring again to the embodiment shown in FIGS. 2A-2B, the insert 20 is comprised of at least two antagonistic materials: a protractor segment 30 and a retractor segment 40. The protractor segment 30 can define a channel 32 that receives a least a portion of the retractor segment 40. In the embodiment shown, the channel 32 can have a suitable cross-sectional shape which helps retain the retractor segment 40 within the channel 32. In the embodiment shown, the retractor segment 40 generally has a T-shape such that opposing arms 42a and 42b of the retractor segment 40 are secured within the channel 32 and are at least partially surrounded by the protractor segment 30.

The protractor segment 30 can be made of a suitable material (for example, a SMA material) that is activated at the subject's body temperature. That is, the protractor segment 30 tends to lengthen the insert 20 when subjected to the subject's body temperature. This lengthening of the protractor segment 30 is such that only a portion of each insert 20 from both ends 21 and 22 straightens, while the remaining central portion 23 contracts and tends to remain firmly gripping the shaft portion 15.

The retractor segment 40 can be made of a suitable material which has an austenite transformation temperature above the body temperature such that the retractor segment 40 can be activated by heating at least the insert 20. Upon heating above the subject's body temperature, the insert 20 retracts, or folds, to the first configuration, thereby allowing the fixation assembly 10 to be easily removed by just unscrewing. The insert 20 thus greatly alleviates potential problems that may be associated with purchase loosening and/or back-out problem in bone screws (for example, due to osteoporosis or to problems that sometimes occur in healthy cancellous bone).

In certain embodiments, the retractor segment 40 can have one or more thread-like ridge members 44 that act like threads to aid in the insertion/removal of the fixation assembly 10. Also, in certain embodiments, the protractor segment 30 can have one or more thread-like ridge members 36 that act like threads to aid in the insertion/removal of the fixation assembly 10.

Figure 3C:
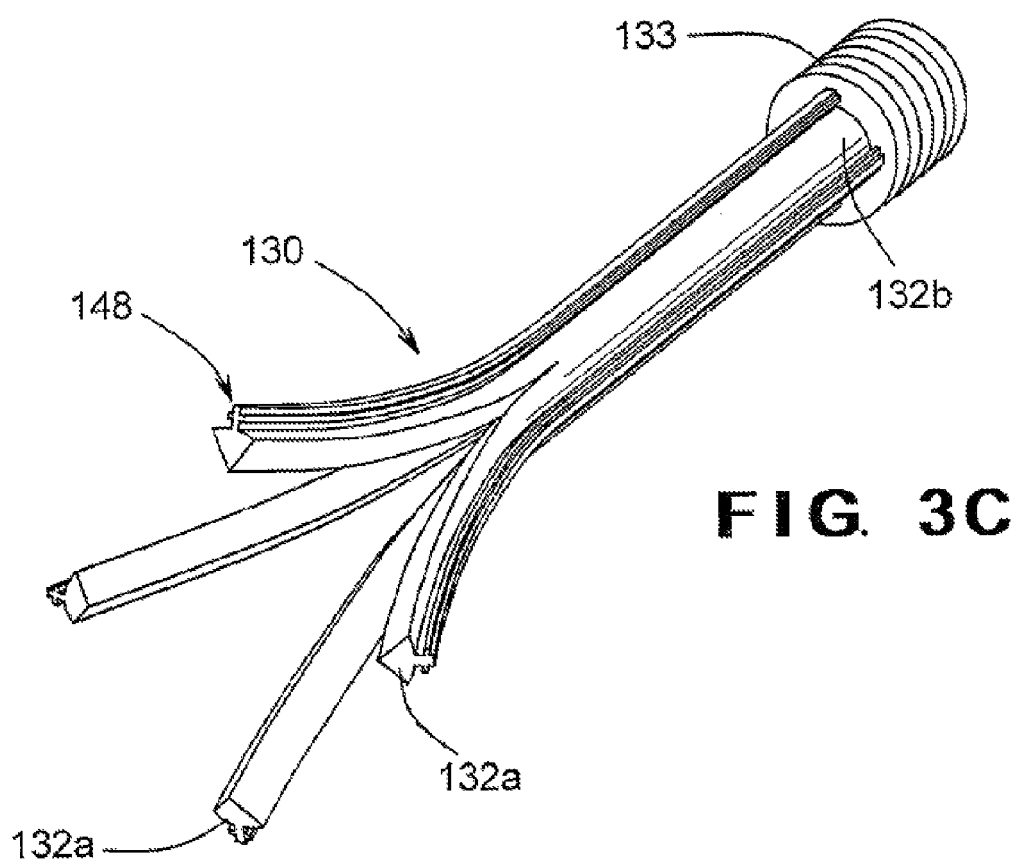
FIG. 3C is a perspective view of an expandable interior anchoring insert of the embodiment of FIG. 3A.

The removable fixation assembly 10 provides a functional implant instrumentation that substantially reduces the risk of stripping of tissues around bone and/or damaging of the bone structure. In certain embodiments, the protractor segment 24 can include one or more ridges Referring now to FIG. 3A, FIG. 3B and FIG. 3C, another embodiment of a fixation assembly 110 is shown. As shown in FIGS. 3A-3B, the fixation assembly 110 includes a outer screw portion 112 comprised of a shaft 114 having helical ridges, grooves or threads 116 formed on an outer surface of the shaft 114. The screw portion 112 has a leading end 117 and a head 118 at an opposing end. It is to be understood that, in certain embodiments, the shaft 114 can be a cylindrical shaft, which in many cases tapers to a point at one end 117 and the head 118 has any suitable shape by which the screw portion 112 can be rotated. The threads 116 can have any desired pitch and can be spaced along the shaft 114 at any desired spacing.

The shaft 114 is comprised of generally longitudinally extending distal sections 136. While the embodiment illustrated in FIGS. 3A-3C show the shaft 114 with four distal sections 136, it is to be understood that fewer or greater numbers of distal sections 136 can be used. The distal section 136 generally includes portions of the threads 116 on an exterior surface thereof, and generally defines at least one channel 138 on an inner surface thereof.

It is to be understood that, in certain embodiments, each channel 138 can have substantially the same dimensions (length, width, cross-sectional shape, overall shape, and the like), while in other embodiments, one or more of the channel 138 can have different dimensions.

Referring now to FIG. 3C, in connection with FIGS. 3A-3B, the fixation assembly 110 further includes an anchoring member 130 which at least partially is positioned within the screw 112. The anchoring member 130 is comprised of one or more generally longitudinally extending legs 132 secured at a proximal end 133. While the embodiment illustrated in FIGS. 3A-3C show an anchoring member 130 with four legs 132, it is to be understood that fewer or greater numbers of legs can be used. For ease of illustration, multiple legs 132 are shown.

It is to be understood that, in certain embodiments, each leg 132 can have substantially the same dimensions (length, width, cross-sectional shape, overall shape, and the like), while, in other embodiments, one or more of the legs 132 can have different dimensions.

Figure 4A:
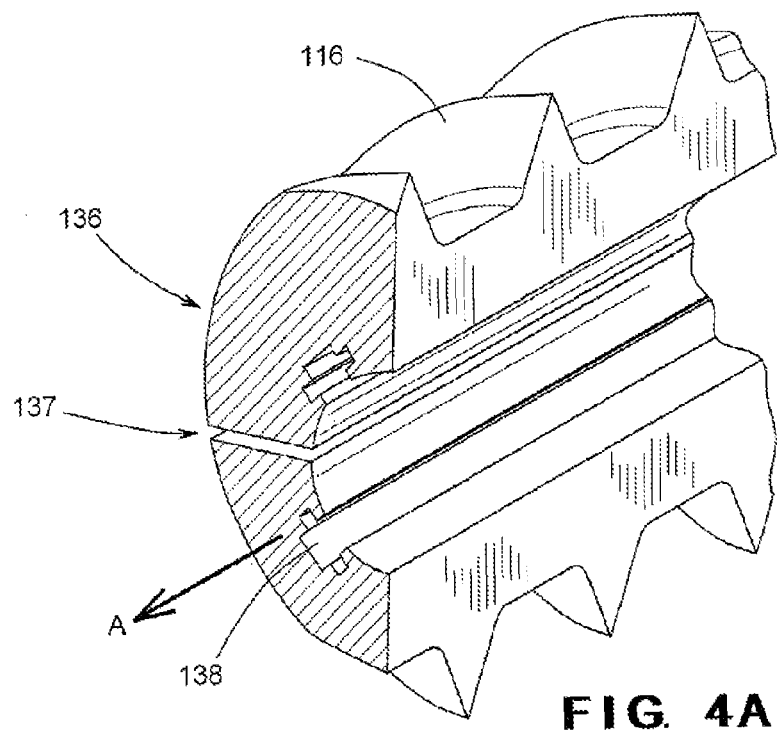
FIG. 4A is a section view of a portion of an expandable exterior anchoring insert of another pedicle screw assembly embodiment.
Figure 4B:
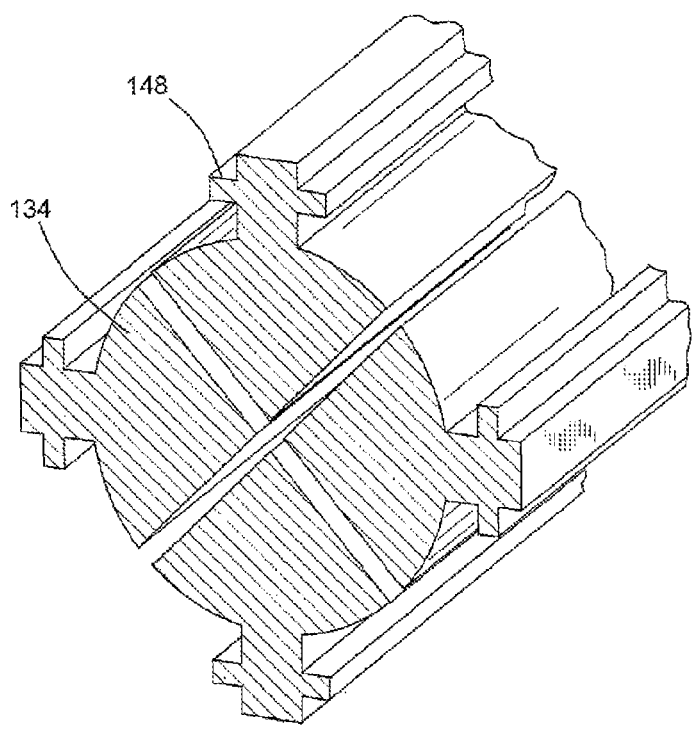
FIG. 4B is a section view of a portion of an expandable interior anchoring insert of another pedicle screw assembly embodiment.

In the embodiment shown in FIG. 4A, the channel 138 is configured to receive at least a portion of an adjacent leg 132 (shown in FIG. 4B). In the embodiment shown, the channel 138 can have a shape which helps retain the leg 132. In the embodiment shown, the distal section 136 at least partially surrounds the leg 132. In one embodiment, the distal section 136 can define a cross-like shaped channel 138 which can then aid in providing engagement of an opposing same-shaped member 148 on the leg 132.

As shown in FIG. 4A, when the fixation assembly 110 is in a contracted configuration, the adjacent distal sections 136 are separated by a longitudinal split 137. The slit 137 allows adjacent distal sections 136 to provide a desired inclined threaded configuration to allow for insertion of the fixation assembly 110.

FIG. 4B shows a cross-sectional perspective view of the distal sections 136 that form a generally cylindrical or closed tapered configuration when in a contracted position. One or more of the legs 132 are made of a material capable of expanding at body temperature and capable of being actuated due to body heat within the subject. Once the fixation assembly 110 is positioned in the bone, the one or more of the legs 132 can extend itself in response to the subject's body temperature. When the fixation assembly 110 is placed in situ, the distal sections 136 continue to augment the screw-bone contact osteoporosis. That is, the legs 132 can continue to expand (in response to body temperature) into areas of the bone that are degraded by osteoporosis and/or the irritating presence of the fixation assembly 110 itself.

This expansion of the legs 132 in a radially outward direction is such that at least a distal portion 141 of the corresponding distal section 136 is moved in a generally radially outward direction away from an axis A defined by the shaft 114. That is, at least a distal portion 132a of the leg 132 is expanded to a greater radial distance than a proximal portion 132b of the leg 132 that is adjacent to the proximal end 133 of the anchoring member 130.

In certain non-limiting embodiments, the distal sections 136 can be comprised of an elastic or superelastic material that has an austenite high temperature form. After placement of the fixation assembly 110 within the subject, the fixation assembly 110 will gradually reach body temperature, thereby expanding the distal sections 136.

If a situation were to arise where the fixation assembly 110 needed to be removed, the temperatures of at least the anchoring member 1309 can be manipulated such that the fixation assembly 110 can be removed. One of the features of the fixation assembly 110 embodiment is that the screw will retract just by pulling out the insert 130 without the need to change the temperature.

The expandable and retractable capabilities of the fixation assemblies described herein provide consistent mechanical contact between the bone and the screw even as the bone gradually degrades due to osteoporosis.

Coated Fixation Assembly

In certain embodiments, the fixation assembly 10 can be used in conjunction with suitable bone cement materials. One non-limiting example of a bone cement is poly methyl methacrylate compensate for lost bone.

In another embodiment, the fixation assembly 10 can be used in conjunction with a suitable biomimetic material, such as a bone growth promoting material, including morphogenic proteins comprised of growth factors and cytokines known for their ability to induce the formation of bone and cartilage; genes coding for production of one or more types of bone cells; and biomimetic minerals. One non-limiting example is a hydroxyapatite (HA) coating or a carbonated calcium deficient hydroxyapatite (CDHA), on at least a portion of the fixation assembly to further improve bonding. The use of HA- or CDHA-coatings can be used to improve the stability of the bone-metal interface without the disadvantages of PMMA and may improve osteointegration and strength at the interface between bone and HA- or CDHA-coated fixation assemblies.

Examples of Useful Shape Memory Alloy Materials

In certain embodiments, the strain that can be recovered through shape memory effect using NiTi as the SMA material is approximately 6-8%. For example, the finite element analysis (FEA) in the embodiment shown in FIG. 3B illustrates that while the legs are opened 60 degrees, the maximum strain is in the order of about 6.6%.

The shape memory alloy materials (SMA) are a group of metallic alloys which exhibit the characteristics of either large recoverable strains or large force due to temperature and/or load changes. The unique thermomechanical properties of the SMAs are due to the phase transformation from the austenite (parent) phase to martensite (product) phase and vice versa. These transformations take place because of changes in the temperature, stress, or a combination of both. In a stress-free state, an SMA material at high temperature exists in the parent phase. The parent or austenite phase usually has a body centered cubic crystal structure. When the temperature of the material decreases the phase transforms into martensite. The martensite phase usually has a face centered cubic structure. In the stress-free state, the martensite phase exists in multiple variants that are similar in orientation of their crystalline structures but are oriented in different habit planes.

From macroscopic point of view, one can separate the observable mechanical behavior of SMAs into two categories: the shape memory effect and pseudoelastic (superelastic) effect. In the shape memory effect, a specimen exhibits a large residual strain after loading and unloading. This strain can be fully recovered upon heating the material. In the pseudoelastic effect, the SMA material provides a large strain upon loading. This strain is fully recovered in a hysteresis loop upon unloading.

When the stress-free austenite phase cools below the martensite start temperature (Ms) the phase starts transforming to martensite. The material will be completely martensitic when the temperature drops below the martensite finish temperature (Mf). In this phase, the material has multiple variants and twins. As long as the temperature of the material is below the austenite start temperature (As), no phase transformation to austenite takes place. However, when this material is loaded, it will initially start deforming elastically. If the stress increases above a certain amount, the pairs of martensite twins begin detwinning to the stress-preferred twins. During this reorientation process, stress rises very slightly and, therefore, the stiffness of the material is at its minimum. This single variant of the martensite is thermodynamically stable at T<As. Therefore, upon unloading there is no conversion to the multiple variant martensite and only a small elastic negative strain will take place. This will leave the detwinned material with a residual strain. The detwinned material can recover the residual strain by heating above the austenite final temperature (Af). The transformation to austenite starts at the austenite start temperature As, thus creating the shape memory effect.

If the temperature is above the martensite start temperature, the material will be in the austenite phase. When the applied stress to this material exceeds a certain amount, the austenite transforms to martensite. This leads to a seemingly plastic strain. The stiffness of the material is at a maximum in the austenite phase. Because of the presence of the stress, upon completion, the material ideally consists of only a single variant of the martensite. If T>Af upon unloading, the material goes through a reverse transformation to the parent phase and thus recovering the strain. The reason for the reverse transformation is that the martensite is not stable at this temperature. The recovery of the strain in the hysteresis loop is called pseudoelasticity. If As<T<Af, the result upon unloading is a partial pseudoelastic strain recovery. The remaining residual strain can be recovered by heating the material above Af. If the material is initially in austenite phase, but T<As upon unloading, no pseudoelastic effect takes place resulting in a different case of shape memory effect.

Thermomechanical Analysis

The thermomechanical behavior of SMAs can be described in terms of strain ($\epsilon$), martensitic fraction ($\xi$), and temperature (T). In the most general form, the thermomechanical constitutive equation is $$d\sigma = D(\epsilon,\xi,T)d\epsilon + \Omega(\epsilon,\xi,T)d\xi + \Theta(\epsilon,\xi,T)dT$$

where $D(\epsilon,\xi,T)$ is representative of the modulus of the SMA material, $\Omega(\epsilon,\xi,T)$ is the transformational tensor, and $\Theta(\epsilon,\xi,T)$ is related to the thermal coefficient of expansion.

The shape memory effect is cause by the phase transformation of the molecular structure between martensite and austenite.

The transformation from austenite to martensite is described by $$\xi = \frac{1-\xi_0}{2}\cos\left[a_m\left(T - M_f - \frac{\sigma}{C_M}\right)\right] + \frac{1+\xi_0}{2}$$

for $M_f + \sigma/C_M < T < A_s + \sigma/C_M$ and $\dot{T} - \dot{\sigma}/C_M < 0$.

The transformation from martensite to austenite is described by $$\xi = \frac{\xi_0}{2}\cos\left[a_A\left(T - A_s - \frac{\sigma}{C_A}\right)\right] + 1$$

for $A_s + \sigma/C_A < T < A_f + \sigma/C_A$ and $\dot{T} - \dot{\sigma}/C_A > 0$, where $\xi_0$ is the martensitic fraction prior to the current transformation, $M_s$ and $M_f$ are the martensite phase start and final temperatures, $A_s$ and $A_f$ are the austenite phase start and final temperatures, and $a_M$ and $a_A$ are defined by $$a_M = \frac{\pi}{M_s - M_f},$$

$$a_A = \frac{\pi}{A_f - A_s}$$

The constants $C_A$ and $C_M$ are material properties that describe the assumed relationship to be linear between temperature and the critical stress to induce transformation.

SMA Heat Transfer

The assumed SMA material heat transfer equation consists of electrical heating and natural convection:

$$mC_p\frac{dT}{dt} = I^2 R - h(T)A_c(T - T_\infty) - m\Delta H\dot{\xi}$$

where m is mass per unit length, $C_p$ is the specific heat, R is resistance per unit length, h(T) is the heat convection coefficient, and $A_c$ is the circumferential area of the SMA material. Also, V is the applied voltage, $T_\infty$ is the ambient temperature, $\Delta H$ is the latent heat, and $\dot{\xi}$ is the phase transformation rate.

Test Data

Figure 5:
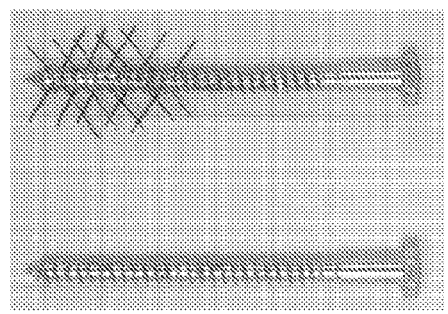
FIG. 5 is a photograph of test screws: control screw (bottom), and test screw (top).

To evaluate the effectiveness of the proposed smart implant a regular screw is retrofitted with superelastic NiTi (Nitinol) elements, as shown in FIG. 5, where a lag screw enhanced with Nitinol superelastic wires (FIG. 5—top). In this test the screw only includes the protractor elements which will be activated by body heat. The 'pullout' performance of the prototype bone screw was tested and compared to that of a regular screw. To simulate the bone, blocks of foam with the density of 15 lb/ft³ were used. Prior to insertion, a hole was drilled and tapped into the block with a diameter of ¼". The size of the hole was selected to be slightly larger to represent worst case scenario to highlight the effectiveness of the fixation assembly described herein. A control specimen (FIG. 5—bottom) was also prepared with exact same specifications but using a regular screw. The specimens were evaluated on a testing machine with a tensile pull-out load applied to the head of the screw. The pulling rate was set to 5 mm/min in accordance with ASTM Standard F543-02.

Figure 6:
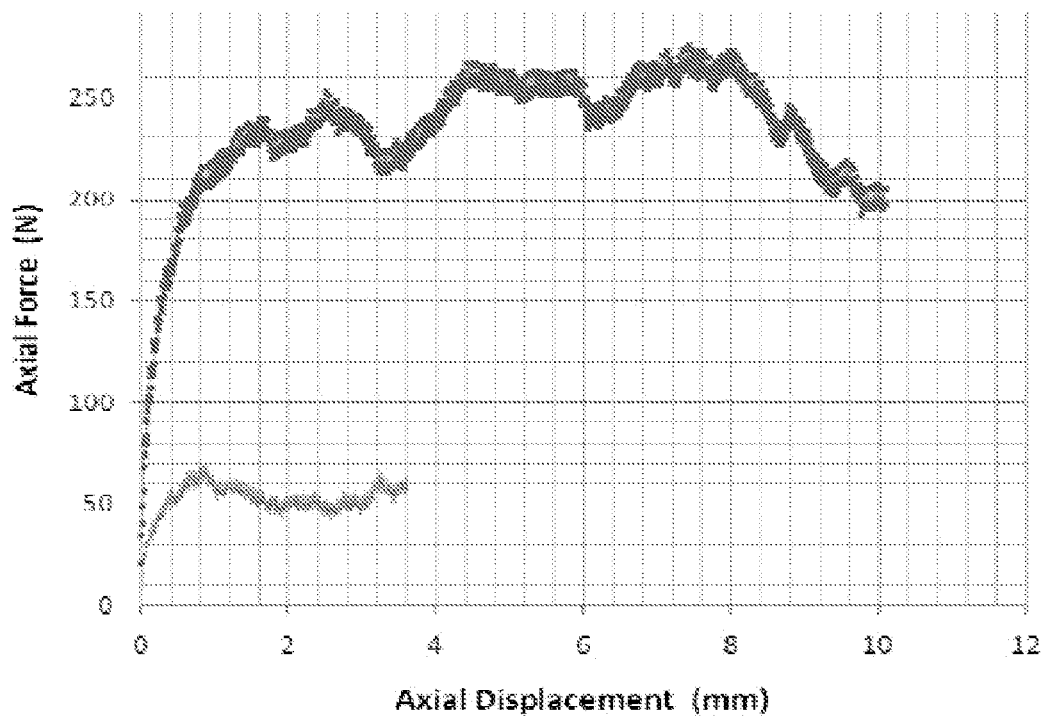
FIG. 6 is a graph showing the axial force v. axial displacement for a control screw (bottom) and test screw (top).

The superior performance of the smart pedicle screw in osteoporotic bones is shown in FIG. 6, which shows the tensile load versus the displacement graph. The mode of failure was rupturing of the material surrounding the screw threads. The load at the instance where the displacement reached equal to the screw pitch (2.85 mm) was chosen as the strengths of the screw. The NiTi smart screw gains resistance again after the displacement reached 3 mm was attributed to the repeated entanglement of the SMA wires with the foam. This is a unique feature, which results in further resistance of the screw against pull-out force; a behavior which could not be seen in the control specimen.

Figure 7:
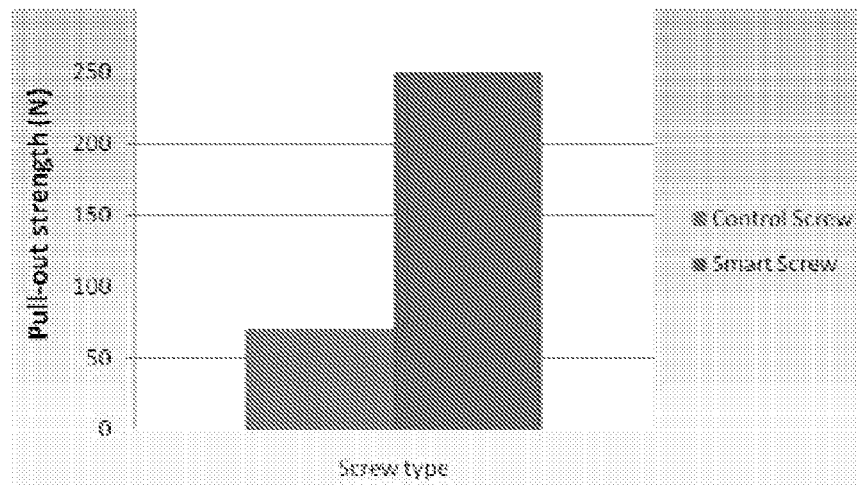
FIG. 7 is a graph showing pull-out strength for control screw (left), and test screw (right).

FIG. 7 shows the results of the axial tensile 'pullout' test: force versus displacement. The tensile strength is selected at the force required to displace the screw in the block as much as the screw thread pitch. The NiTi smart screw provides superior (~5 times) pullout strength and fixing-range in osteoporotic bone.

Other Exemplary Uses

In other embodiments, the fixation assembly to industrial purposes where a structure should be attached to a softer or degradable base.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, any means-plus-function clauses are intended to cover the structures described herein as performing the recited function and not only structural equivalents but also equivalent structures.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A fixation assembly comprising at least one insertion member that includes one or more expandable and retractable anchoring inserts positioned along at least a portion of the insertion member;
   the insertion member comprising a screw having a shaft with a helical thread formed on at least a portion of an outer surface of the shaft; and,
   one or more of the expandable and retractable anchoring inserts being positioned along at least a portion of the shaft between one or more adjacent helical threads,
   the anchoring insert being comprised of at least two antagonistic materials: a retractor segment and a protractor segment,
   at least a portion of the protractor segment being comprised of a material that expands or contracts in response to an appropriate change in temperature, and
   at least a portion of the retractor segment being comprised of a material which has an austenite transformation temperature different from the temperature at which the protractor segment expands or contracts;
   wherein the protractor segment defines a channel that receives at least a portion of the retractor segment.

2. The fixation assembly of claim 1, wherein at least one of the retractor segment and protractor segment comprises at least one shape memory allow or superelastic material.

3. The fixation assembly of claim 2, wherein the at least one shape memory allow material is comprised of NiTi.

4. The fixation assembly of claim 1, wherein at least a portion of the shaft is coated with a bone growth promoting material.

5. The fixation assembly of claim 1, wherein at least one of the protractor segment or the retractor segment has first and second opposing ends configured to be expanded in a tangential manner with respect to the shaft when exposed to a change in temperature.

6. The fixation assembly of claim 1, wherein the retractor segment has a T-shape cross-section having opposing arms that are secured within the channel and are at least partially surrounded by the protractor segment.

7. The fixation assembly of claim 1, wherein the material comprising the protractor segment is comprised of a material that is activated at the subject's body temperature such that the protractor segment lengthens the insert when subjected to the subject's body temperature.

8. The fixation assembly of claim 1, wherein the material comprising the retractor segment is comprised of a material which has an austenite transformation temperature above the body temperature such that the retractor segment can be activated by heating or cooling at least the insert.

9. The fixation assembly of claim 1, wherein the retractor segment has one or more longitudinally extending thread-like ridge members.

10. The fixation assembly of claim 1, wherein the protractor segment has one or more longitudinally extending thread-like ridge members.

11. The fixation assembly of claim 1, wherein the fixation assembly comprises a bone fixation assembly.

12. The fixation assembly of claim 1, wherein the fixation assembly comprises a pedicle screw fixation assembly.

13. The fixation assembly of claim 1, wherein the temperature at which the protractor expands or contracts is a human body temperature.

14. A method of inserting a fixation assembly, comprising:
   providing a fixation assembly of claim 1;
   inserting at least a portion of the fixation assembly into an object; and
   exposing at least a portion of the fixation assembly to a change in temperature sufficient to cause at least a portion of the fixation assembly to change dimensionally, whereby at least a portion of the fixation assembly is secured within the object.

15. The method of claim 14, wherein the object comprises bone.

16. The method of claim 15, wherein the bone comprises vertebral bone.

* * * * *